US005512069A

United States Patent [19]
Holland et al.

[11] Patent Number: 5,512,069
[45] Date of Patent: Apr. 30, 1996

[54] SEEDS, COATED OR IMPREGNATED WITH A PPFM

[75] Inventors: Mark A. Holland, Salisbury, Md.; Joseph C. Polacco, Columbia, Mo.

[73] Assignees: Salisbury State University, College Park, Md.; The Curators of the University of Missouri, Columbia, Mo.

[21] Appl. No.: 414,385

[22] Filed: Mar. 31, 1995

[51] Int. Cl.⁶ .................................................. A01N 63/00
[52] U.S. Cl. ...................... 47/57.6; 424/93.1; 435/240.47
[58] Field of Search ................... 47/57.6, 58; 424/93.1, 424/93.3, 93, 47; 435/240.47, 240.54

[56] References Cited

U.S. PATENT DOCUMENTS

| | | | |
|---|---|---|---|
| 4,061,488 | 12/1977 | Mann | 47/57.6 |
| 4,417,417 | 11/1983 | Mehra-Palta | 435/240.54 |
| 4,456,684 | 6/1984 | Weller et al. | 424/93.47 |
| 4,798,723 | 1/1989 | Dart et al. | 47/57.6 |
| 4,849,008 | 7/1989 | Schroth | 435/877 |
| 4,977,087 | 12/1990 | Koulin et al. | 435/240.47 |
| 4,992,375 | 2/1991 | Wright | 435/240.54 |
| 5,106,648 | 4/1992 | Williams | 47/57.6 |
| 5,244,658 | 9/1993 | Parke | 424/93.47 |
| 5,268,171 | 12/1993 | Polacco et al. | 47/57.6 |
| 5,415,672 | 5/1995 | Fohey | 47/57.6 |

OTHER PUBLICATIONS

Kiyoshi Tsuji, et al. (1990) "16S ribosomal RNA sequence analysis for determination of phylogenetic relationship among methylotrophs" *Journal of General Microbiology* vol. 136, pp. 1–10.

*Primary Examiner*—James R. Feyrer
*Attorney, Agent, or Firm*—Oblon, Spivak, McClelland, Maier, & Neustadt

[57] ABSTRACT

Seeds coated or impregnated with at least one pink pigmented facultative methylotroph (PPFM) have improved germinability. PPFMs can be cultured to produce the cytokinin zeatin.

6 Claims, No Drawings

SEEDS, COATED OR IMPREGNATED WITH A PPFM

BACKGROUND OF THE INVENTION

1. Field of the Invention

The present invention relates to seeds, coated or impregnated with a Pink Pigmented Facultative Methylotroph (PPFM), which seeds have improved germinability. Also, the present invention relates to a method of producing zeatin using PPFMs.

2. Discussion of the Background

Improvements in crop yields is a highly active area of research, and as a result, today's farms are much more productive than their counterparts from a century ago. However, as the world's population increases with a concomitant decrease in farming resources, more and more emphasis is being placed on enhancing crop yields. Farmers are presently seeking ways to expand their yields while limiting the use of dangerous fertilizers and pesticides. An avenue of research which has developed from the desire to avoid harmful chemical crop treatments is the treatment of seeds or the soil with non-toxic crop augmenter prior to sowing.

Schroth et al, U.S. Pat. No. 4,849,008, describes enhancing root crop yields by treating plant seeds with a specific growth promoting bacterial strain of the genus Pseudomonas. The bacterial strains may be applied with a liquid carrier or in a paste.

Williams, U.S. Pat. No. 5,106,648, refers to a method of preparing coated seeds by slurrying seeds with a microorganism, which has a beneficial effect on plants which grow from these seeds, a carrier medium and an adhesive polymer. This method is supposed to maintain microorganisms viable for extended periods of time.

Mann, U.S. Pat. No. 4,061,488, addresses treatment of plant seeds with spores from *Bacillus uniflagellatus* to enhance plant growth. It is suspected that root growth triggers the germination of these spores.

The patents described above report enhancement of the growth of a plant, but do not address the problem of less than 100% seed germination. If a seed does not germinate, then no amount of plant growth improvement can be obtained. Low rates of germination are a problem with certain plant species in particular and with old seed in general. If a farmer were able to escalate the number of planted seeds which germinate, then an increase in crop production would be obtained. It is thus desirable to improve the germinability of seeds. Additionally, these references do not address addition of PPFMs to tissue cultures, for plant regeneration, embryo culture or rescue or propagation of cuttings or other propagules.

A further development in plant research is the use of cytokinins (e.g., benzyladenine or zeatin) to alter the growth and regeneration of plant cell cultures. Regulating the amount of cytokinin in a plant cell culture is necessary if regeneration of whole plants from the culture is desired. The ability to regenerate plants from cell culture develop new plant lines which may have novel physical characteristics such as pest resistance following gene transfer or mutagenesis by genetic engineering protocols.

Koulin et al, U.S. Pat. No. 4,977,087, depicts a method of regenerating plantlets from protoplasts cultured in liquid media containing cytokinins and/or auxins. Both zeatin and 6-benzyl-aminopurine (benzyladenine) are used in the culture media.

Mehra-Palta, U.S. Pat. No. 4,417,417, describes propagation of plantlets in the presence of a cytokinin (e.g. zeatin and 6-benzyl-aminopurine) and optionally an auxin.

Wright, U.S. Pat. No. 4,992,375, characterizes regeneration of soy bean plants using a nutrient medium containing a cytokinin (e.g. benzyladenine). Nodes used for regeneration were obtained by sterilizing soy bean seeds and germinating them in the presence of benzyladenine.

None of these references suggest the use of cytokinins as germination improvers. Additionally, PPFMs can be used advantageously in specific plant tissue culture processes. Further, zeatin is a costly chemical which cost has limited large scale use. It is thus desirable to find a novel method of producing zeatin.

SUMMARY OF THE INVENTION

These goals of the prior art, and others discussed below, are achieved by the coating or impregnation of plant seeds with PPFMs or cytokinins (such as zeatin) produced by PPFMs.

These and other objects, which will become apparent during the following detailed description, have been achieved by the inventors' discoveries that seeds coated or impregnated with a germinability improving effective amount of at least one PPFM have improved germinability and that PPFMs produce zeatin. Further, because they produce cytokinin, because they consume toxic methanol generated by growing plant cells, because they are normally associated with all plants, and because they produce other substances (like vitamin $B_{12}$) which may be beneficial to the plant, the use of PPFMs in plant tissue culture can improve the performance of the culture.

DETAILED DESCRIPTION OF THE PREFERRED EMBODIMENTS

In a first embodiment, the present invention provides novel seeds coated with a germinability improving effective amount of at least one PPFM.

PPFMs have been reported from virtually all land plants examined. Corpe, W. A., J. Microbiol. Methods, 3:215–221 (1985). Members of all eight plant phyla contain associated PPFMs. While other non-pink methylotrophs are also associated with plants, PPFM's are the most persistent and become the predominant phylloplane methylotrophs when leaf surfaces are washed.

The inventors have found PPFM's in all soybean tissues, including seed and callus, at $\geq 10^6$ cfu-g $fw^{-1}$ and classify PPFMs as Methylobacterium spp., not only by their methylotrophy and pink pigmentation, but also due to restriction analysis of PCR-amplified 16S rRNA genes. Tsuji et al., J. Gen. Microbiol. 136:1–10 (1990). PPFMs isolated from soybean most closely resemble *M. mesophilicum* while isolates from other plants group include such members as *M. organophilum* and *M. extorquens*. Thus, the term PPFM as used herein is intended to encompass all pink pigmented facultative methylotroph bacteria.

In a preferred embodiment, the PPFM contained in the coating is at least one PPFM selected from the group consisting of *M. mesophilicum*, *M. organophilum* and *M. extorquens*. In a more preferred embodiment, *M. mesophilicum* is contained in the coating.

The coated seeds according to the present invention can be formed using known coating procedures like that shown in U.S. Pat. No. 5,106,648, the contents of which are incorporated herein by reference. For example, the coated seeds may be prepared by slurrying seeds with a coating composition containing a suspension of at least one PPFM in water and air drying the resulting product, preferably at a temperature not greater than 30° C. The proportion of coating to seed may be selected from the range of 0.1 to 25% by weight of the seed, preferably, 0.5 to 5% by weight and most preferably 0.5 to 2.5% by weight, depending on the type of seed. For a coating composition, the polymeric adhesive preparation of U.S. Pat. No. 5,106,648 may be used. Thus, a carrier such as peat or vermiculite, the bacteria, and an adhesive polymer of, e.g., vinyl pyrrolodine-vinyl acetate copolymer can be applied.

Viable PPFMs should be present in the coating in an amount effective to increase the germinability of a seed lot (e.g., 50 seeds) by at least 5% compared with an uncoated seed lot. Preferably, viable PPFMs should be present in an amount effective to increase the germinability of a seed lot by at least 10% compared with an uncoated seed lot. More preferably, viable PPFMs should be present in an amount effective to increase the germinability of a seed lot by at least 15% compared with an uncoated seed lot. Most preferably, viable PPFMs should be present in an amount effective to increase the germinability of a seed lot by at least 20% compared with an uncoated seed lot. In preferred coatings, bacterial concentration of $10^5$–$10^{10}$ bacterial cells/ml is considered a desirable range, although optimum values for specific seeds and bacteria may be empirically determined.

In a second embodiment, the present invention provides novel seeds impregnated with a germinability improving effective amount of at least one PPFM.

In a preferred embodiment, the PPFM impregnated is at least one PPFM selected from the group consisting of $M.$ $mesophilicum$, $M.$ $organophilum$ and $M.$ $extorquens$. In a more preferred embodiment, $M.$ $mesophilicum$ is impregnated in the seed.

The impregnated seeds can be obtained by immersing seeds in a PPFM-enriched solution such that the PPFM enters the seed and then planting the seed or drying the seed for later planting. Alternatively, PPFMs could be delivered by vacuum infiltration or under pressure. The term impregnated as used herein means that the PPFM is contained inside at least the outer seed coat of the seed. Impregnation of the seed can best be achieved by immersion of dry seed in a solution comprising deionized, sterilized water and the bacteria, followed by planting or air drying.

The amount of viable PPFMs impregnated in the seed should be sufficient to increase the germinability of a seed lot (e.g., 50 seeds) by at least 5% compared with an uncoated seed lot. Preferably, the amount of viable PPFMs should be sufficient to increase the germinability of a seed lot by at least 10% compared with an uncoated seed lot. More preferably, the amount of PPFMs should be sufficient to increase the germinability of a seed lot by at least 15% compared with an uncoated seed lot. Most preferably, the amount of PPFMs should be sufficient to increase the germinability of a seed lot by at least 20% compared with an uncoated seed lot. To achieve this goal, an aqueous preparation of $10^7$–$10^8$ bacterial cells/ml should be used for soy bean seeds.

As noted, plant growth and plant growth regulation can also be effected by conducting plant tissue culture in the presence of cytokinins such as zeatin. Thus, U.S. Pat. No. 4,417,417, which is incorporated-herein-by-reference describes propagation of plantlets on a nutrient medium which contains 10 mg/L of a cytokinin such as zeatin. Lack of control over the time and concentration of appropriate cytokinin exposure, difficulties in maintaining a continous and stable concentration of cytokinins and the like in the media have made it difficult to take full advantage of this alternative.

The inventive discoveries herein include the observation that introduction of exogenous cytokinins can be advantageously replaced or supplemented by tissue plant culturing in the presence of PPFMs. These bacteria can grow on a wide variety of media, including those most commonly employed in tissue culture plant growth, such as basal nutrient media (mineral salts, organic nutrients and plant hormones) or augmented media which include additional sources such as sucrose, inositols and thiamine. Various PPFMs express zeatin and possibly other cytokinins and growth-enhancing substances in varying amounts. In general, the presence of sufficient PPFM to generate a concentration of $10^3$–$10^7$ bacterial cells/ml of culture media is sufficient. PPFM presence can be used to augment tissue culture for plant propagation by organogenesis, embryogenesis, embryo culture or embryo rescue as the most appropriate for this invention, or for propagation of cuttings or other propagules. It is important to note in this regard that applicants' discovery is based on the recognition that cytokinins are not plant growth products (at least not exclusively) and are produced by PPFMs. Applicants' discovery further resides in the recognition that tissue culture growth of the type identified advantageously practiced in the presence of PPFMs.

In another embodiment, the present invention provides a novel method of producing zeatin which involves culturing at least one PPFM type. PPFMs can be cultured in a minimal salts medium, with methanol as sole carbon source, using standard fermentation technology, followed by collection of the zeatin by cell harvesting, media fractionation and standard isolation techniques such as TLC or HPLC to give adequate recovery of zeatin at a reduced cost. Cytokinin production and expression can be further enhanced by the addition of a plant extract, to the medium, although such addition is not required.

Other features of the invention will become apparent in the course of the following descriptions of exemplary embodiments which are given for illustration of the invention and are not intended to be limiting thereof.

EXAMPLES

To study the effect of PPFMs on seed germination, soybean seeds were heat-treated at 50° C. for 48 h to reduce the populations of PPFMs (31). Five different treatments using both heated and unheated seeds were then performed:

(1) imbibition in sterile water;

(2) imbibition in PPFM culture medium (salts only);

(3) imbibition in spent PPFM culture medium (i.e. complete PPFM medium in which PPFMs were grown to stationary phase, filtered through a 0.45 mm filter to remove bacterial cells);

(4) imbibition in PPFM culture medium (salts only) plus cytokinins (0.5 mg/L BA and 0.5 mg/zeatin); and, (5) imbibition in a suspension of washed PPFM cells.

After imbibition, the seeds were allowed to germinate on sterile germination paper. After four days, the percent germination of the seeds was determined and the results are given in Table 1 below. Each entry represents the mean germination percentage of two trials, each of which included 50 seeds. The preferred medium is sterilized water as a carrier for the bacteria.

TABLE 1

Effects of PPFM bacteria on germination of soybean seeds.

| Treatment | Unheated | Heated |
|---|---|---|
| (1) Water | 96% | 70% |
| (2) PPFM Medium[a] | 95 | 70 |
| (3) Spent Medium[b] | 95 | 79 |
| (4) Medium + BA + Zn[c] | 100 | 87 |
| (5) Washed PPFMs[d] | 98 | 86 |

[a]Ammonium Mineral Salts (AMS) medium (31) without carbon or nitrogen sources added.
[b]Complete AMS medium in which PPFMs have grown to stationary phase.
[c]AMS medium without carbon or nitrogen, but containing 0.5 mg/L benzyl adenine and 0.5 mg/L zeatin.
[d]PPFMs harvested from spent medium above by centrifugation, resuspended in sterile water, recentrifuged, and resuspended in sterile water (final volume equivalent to volume on initial culture).

The effect of PPFMs on the germinability of fresh and old lots of *Carthamus tinctorius* safflower seeds treated with PPFMs was studied. The seeds were impregnated with PPFM by imbibing the seeds in sterilized, distilled water containing the PPFMs after which treatment they were allowed to germinate. Bacterial concentration was approximately $10^7$ bacterial cells/ml. Old seed and fresh seeds differed only in respect to age (and in age-correlated rate of germination). That is, all seeds were of the same genetic background, but old seed showed decreased germination compared to fresh seed. The seeds were obtained from the National Seed Storage Laboratory at Fort Collins, Colo. The germination percentages of untreated and treated seeds are given in Table 2 below.

TABLE 2

Effects of PPFM bacteria on germination of *Carthamus tinctorius* safflower seeds.

| Seed Age | PPFM Treatment? | % germination |
|---|---|---|
| Fresh | No | 75 |
| Fresh | Yes | 87 |
| Old | No | 18 |
| Old | Yes | 38 |

Thus, a 16% increase in germination percentage was observed with fresh safflower seeds treated with a PPFM compared with an untreated fresh seed and a 122% increase was observed with treated old safflower seeds compared with untreated old seeds.

Obviously, numerous modifications and variations of the present invention are possible in light of the above teachings. In particular, variations in PPFM identity, concentration and media characterization will occur to those of skill in the art without the exercise of inventive skill. Such variation remains within the scope of the invention, save as limited by the recitation of the claims set forth below. It is, therefore, to be understood that within the scope of the appended claims, the invention may be practiced otherwise than as specifically described herein.

What is claimed as new and desired to be secured by Letters Patent of the United States is:

1. A coated seed having improved germinability, comprising:

(a) a seed; and, (b) a coating, comprising: a cytokinin producing, germinability improving effective amount of at least one pink pigmented facultative methylotroph (PPFM), of natural genetic origin wherein said coating is disposed on the outer surface of said seed.

2. The coated seed according to claim 1, wherein said PPFM is selected from the group consisting of *M. mesophilicum M. organophilum* and *M. extorquens*.

3. The coated seed according to claim 1, wherein said seed is comprises of soybean seeds.

4. A bacterium impregnated seed having improved germinability, comprising:

(a) a seed; and (b) at least one cytokinin producing pink pigmented facultative methylotroph (PPFM) of natural genetic origin, wherein said PPFM is disposed inside the outer seed coat of said seed.

5. The impregnated seed according to claim 4, wherein said PPFM is selected from the group consisting of *M. mesophilicum M. organophilum* and *M. extorquens*.

6. The impregnated seed according to claim 4, wherein said seed comprises soybean seeds.

* * * * *